United States Patent [19]

Kahlert et al.

[11] Patent Number: 4,639,423

[45] Date of Patent: Jan. 27, 1987

[54] APPARATUS FOR THE PRODUCTION OF BIOCATALYST BEADS

[75] Inventors: Wolfgang Kahlert, Melsungen; Joachim Klein, Braunschweig; Hans-Jürgen Steinert, Illsede; Claus Vorlop, Braunschweig, all of Fed. Rep. of Germany

[73] Assignee: Intermedicat GmbH, Emmenbruck, Switzerland

[21] Appl. No.: 667,361

[22] Filed: Nov. 1, 1984

[30] Foreign Application Priority Data

Nov. 3, 1983 [DE] Fed. Rep. of Germany ....... 3339764

[51] Int. Cl.$^4$ .............................................. C12M 1/00
[52] U.S. Cl. ..................................... 435/287; 435/311
[58] Field of Search ............... 435/311, 287, 259, 289

[56] References Cited

U.S. PATENT DOCUMENTS 4,435,505 3/1984 Zierdt ................................. 435/287

OTHER PUBLICATIONS

*Immobilized Cells* Catalyst Preparation and Reaction Performance, J. Klein et al., ACS Symposium, American Chemical Society, Series 207, pp. 377-392, 17, 1983.

*Primary Examiner*—James C. Yeung
*Attorney, Agent, or Firm*—Kenyon & Kenyon

[57] ABSTRACT

An apparatus for the production of biocatalyst beads comprises an immobilization vessel (10) which is provided at its lower end with discharge pipes (23) which extend through a pressure chamber (25) in which a gas pressure prevails. The pressure chamber (25) is terminated by a plate (24) exhibiting holes which coaxially surround the discharge pipes (23). At the lower end of the immobilization vessel (10) is provided a connecting nozzle (30) which is connected in germproof sealing manner to the wall of a collecting vessel (11) which contains a solution of a cross-linking agent or a re-precipitation bath. The collecting vessel (11) may be constructed as a fermenter and provided with an agitator. Both of the vessels may be jointly sterilized.

14 Claims, 5 Drawing Figures

APPARATUS FOR THE PRODUCTION OF BIOCATALYST BEADS

FIELD OF THE INVENTION

This invention relates to an apparatus for the production of biocatalyst beads, comprising an immobilization vessel which is sealed in a germproof manner and exhibits in its upper region at least one filling tube and, in its lower region, discharge pipes which extend through a pressure chamber which exhibits discharge openings arranged coaxially to the discharge pipes; and a collecting vessel or receiver arranged beneath the immobilization vessel and containing a solution of a cross-linking agent or a reprecipitation bath.

BACKGROUND OF THE INVENTION

Immobilized cells are effective catalysts in the enzymatic conversion of organic ingredients. It is known to effect the immobilization of cells by introducing the cells together with a supporting substance into a polymer solution which is capable of gelling and then runs out with formation of drops from the immobilization vessel and falls into a collecting vessel which contains a solution of a cross-linking agent (J. Klein and K.-D. Vorlop (1983) ACS Symposium Series 207, 377–392; American Chemical Society, 1983, 17). The drops are formed by supplying sterile compressed air coaxially to the discharge pipes coming out of hte immobilization vessel, said compressed air sweeping along the discharge pipes and facilitating the shaping and detachment of the discharge pipe. While freely falling down and being cross linked, the drops assume the shape of balls or beads so that biocatalyst beads in the form of balls are present in the collecting vessel.

It is of particular importance when immobilizing cells to maintain them sterile before and during the immobilization process. When using the known apparatus, it is necessary to separately pre-sterilize all of the parts and thereafter use them in a sterile atmosphere.

OBJECTS AND SUMMARY OF THE INVENTION

It is an object of the present invention to provide an apparatus of the type mentioned above and facilitating the production of biocatalyst beads under sterile conditions.

To accomplish this object, it is provided in accordance with the invention that the immobilization vessel exhibits a lower connecting nozzle surrounding the entirety of the discharge pipes and that the collecting vessel is sealed in a germproof manner and is provided with a cover with an opening for the sealed connection of the connecting nozzle.

The immobilization vessel forms together with the collecting vessel an assembly which is capable of being sterilized as a total and, when in use, contaminations by the ambient air cannot take place especially in the transition region between the immobilization vessel and the collecting vessel. However, both of the vessel may yet be manufactured separately and also be cleaned or used for other purposes separately. The microorganisms or enzymes which are occluded in the biocatalyst beads do not contact the atmosphere even during the free fall into the solution of the cross-linking agent or into the reprecipitation bath so that the entire procedure takes place under germproof conditions.

The collecting vessel may be constructed as fermenter and provided with an agitator and/or a heater. It is possible in this manner to use the collecting vessel simultaneously for the further processing of the biocatalyst beads without the necessity of still transferring the latter into another vessel after having been produced.

According to a preferred further development or embodiment of the invention, it is provided that the discharge pipes are attached in a dismountable annular insert of the immobilization vessel, which insert is provided with an upper perforated plate having fitted in the holes thereof the upper ends of the discharge pipes and with a lower plate which is arranged at a distance to the upper perforated plate and in which the outflow openings are arranged. The annular insert forms in this case a dismountable member which is capable of being removed from the immobilization vessel for the purpose of being cleaned and attended. The space between the upper perforated plate and the lower plate constitutes the pressure chamber into which a sterile gas is introduced which escapes through the lower outflow openings coaxially to the discharge pipes and assists the detachment of drops at the lower ends of the discharge pipes as well as determines the size of the drops.

The insert is preferably surrounded by an annular space connected to a pressure source and exhibits in its wall openings which lead from the annular space into the interior of the insert. This ensures uniform action of pressure on the pressure chamber while the sterile compressed gas is distributed in the annular space outside the insert. Uniform distribution of pressure of the flowing compressed gas is particularly important for achieving uniform sizes of the biocatalyst beads.

Preferably the discharge pipes protrude into the interior of the collecting vessel to below the cover. Thus, the discharge pipes protrude to beyond the lower end of the immobilization vessel so that the detachment of the drops takes place in the interior of the collecting vessel.

The construction of the apparatus for the production of biocatalysts can be simplified by the fact that the immobilization vessel exhibits an agitator extending from above into its inside space or is provided with a heater. It is possible in this manner that the immobilization vessel is used at the same time as a mixing vessel into which the supporting substance and the enzymes or microorganisms are separately introduced while the mixing takes place in the interior of the immobilization vessel. This saves an additional mixing vessel for preparing the immobilization. To be able to introduce the enzymes or microorganisms into the immobilization vessel under sterile conditions, the immobilization vessel is provided at the upper end with an innocculating nozzle with a pierceable septum.

BRIEF DESCRIPTION OF THE DRAWINGS

Working examples of the invention are illustrated hereafter in greater detail with reference to the drawings where.

DETAILED DESCRIPTION

Figure 1:
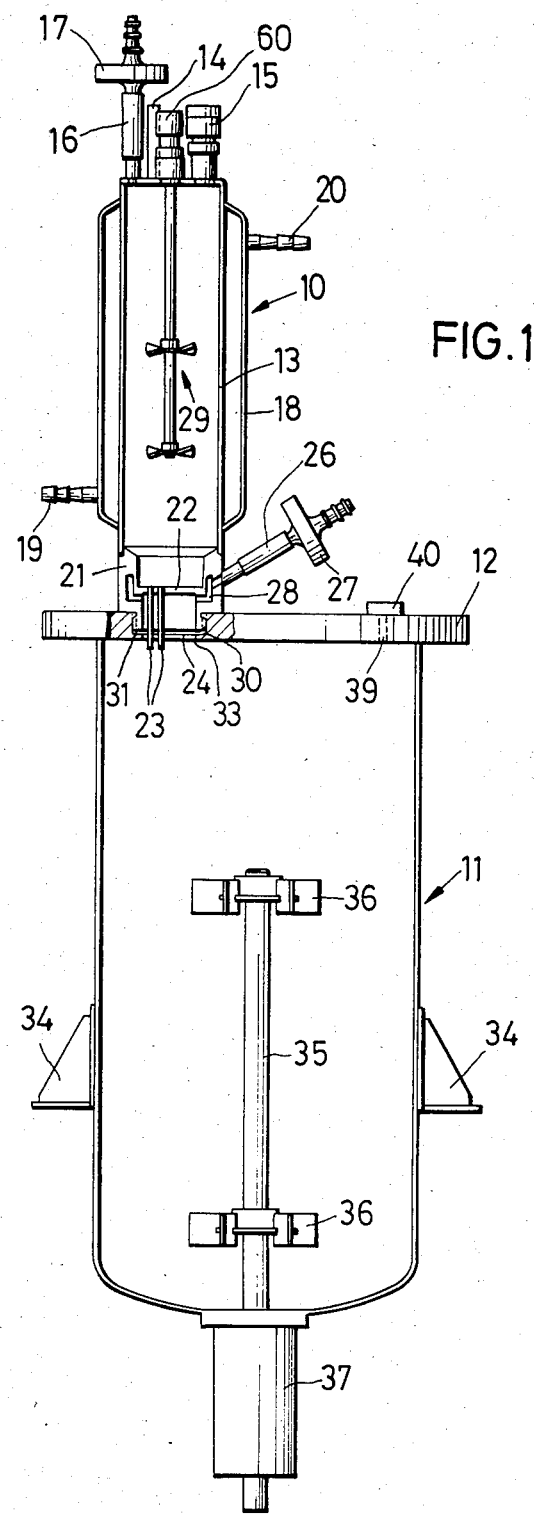
FIG. 1 shows a longitudinal section through a combination consisting of an immobilization vessel and a collecting vessel.

According to FIG. 1, the immobilization vessel 10 is fixedly mounted on the cover 12 of the collecting vessel 11. The immobilization vessel 10 consists of a vertical tubular container 13, in the upper end wall of which are arranged a closable feed nozzle 14, an inocculating nozzle 15 provided with a septum which is pierceable with a hollow needle, and a gas inlet 16 with a filter 17. The feed nozzle 14 and the gas inlet 16 are nozzles which are identically constructed and which may also be exchanged with respect to their functions of used for other purposes.

The peripheral wall of the container 13 is surrounded by a heating device 18 in the form of a heating jacket which is provided with an inlet nozzle 19 and an outlet nozzle 20 for a heating medium. The lower end of the container 13 is closed by a block 21. The block 21 is provided with a horizontal perforated plate 22 which forms the lower bottom wall of the container 13 and into the holes of which the upper ends of a great number of vertical discharge pipes 23 are fitted. The discharge pipes 23 extend through holes of a lower plate 24 downwardly into the interior of the collecting vessel 11. Between the plates 22 and 24 is formed a pressure chamber 25 into which a sterile gas is introduced through a gas inlet nozzle 26 with a filter 27. The gas inlet nozzle 26 extends into the annular space 28 in the interior of the block 21. Bores extend from the annular space 28 into the pressure chamber 25.

In the interior of the vessel 13 is arranged an agitator 29 which is either connected with an electrical drive mechanism outside the vessel 13 or may be rotated manually from the outside at a rotary knob 60. The agitator consists of a shaft of agitator and stirring vanes attached to said shaft.

The lower end of the block 21 of the immobilization vessel 10 is constructed as a threaded nozzle 30. The threaded nozzle 30 is inserted by threading into a threaded bore of the cover 12. A packing 31 seals the passage through the opening 33 of the cover 12.

The collecting vessel 11 having a volume which is substantially greater than that of the immobilization vessel 10 also consists of a tubular container which is provided at its outer wall with holders 34 for the attachment to a supporting device. Through the bottom wall of the collecting vessel 11 extends a shaft 35 of agitator to which stirrer vanes 36 are attached and which can be driven by a motor 37 arranged outside the collecting vessel 11. Additionally, the collecting vessel 11 may be heatable. In the present case, it is constructed as a fermenter. Superatmospheric pressure may escape from the collecting vessel 11 through a vent opening 39 with a filter 40.

In the mounted state represented, the assembly shown in FIG. 1 and comprising the immobilization vessel 10 and collecting vessel 11 can be sterilized as a whole. Its use will still be explained in greater detail farther below.

Figure 2:
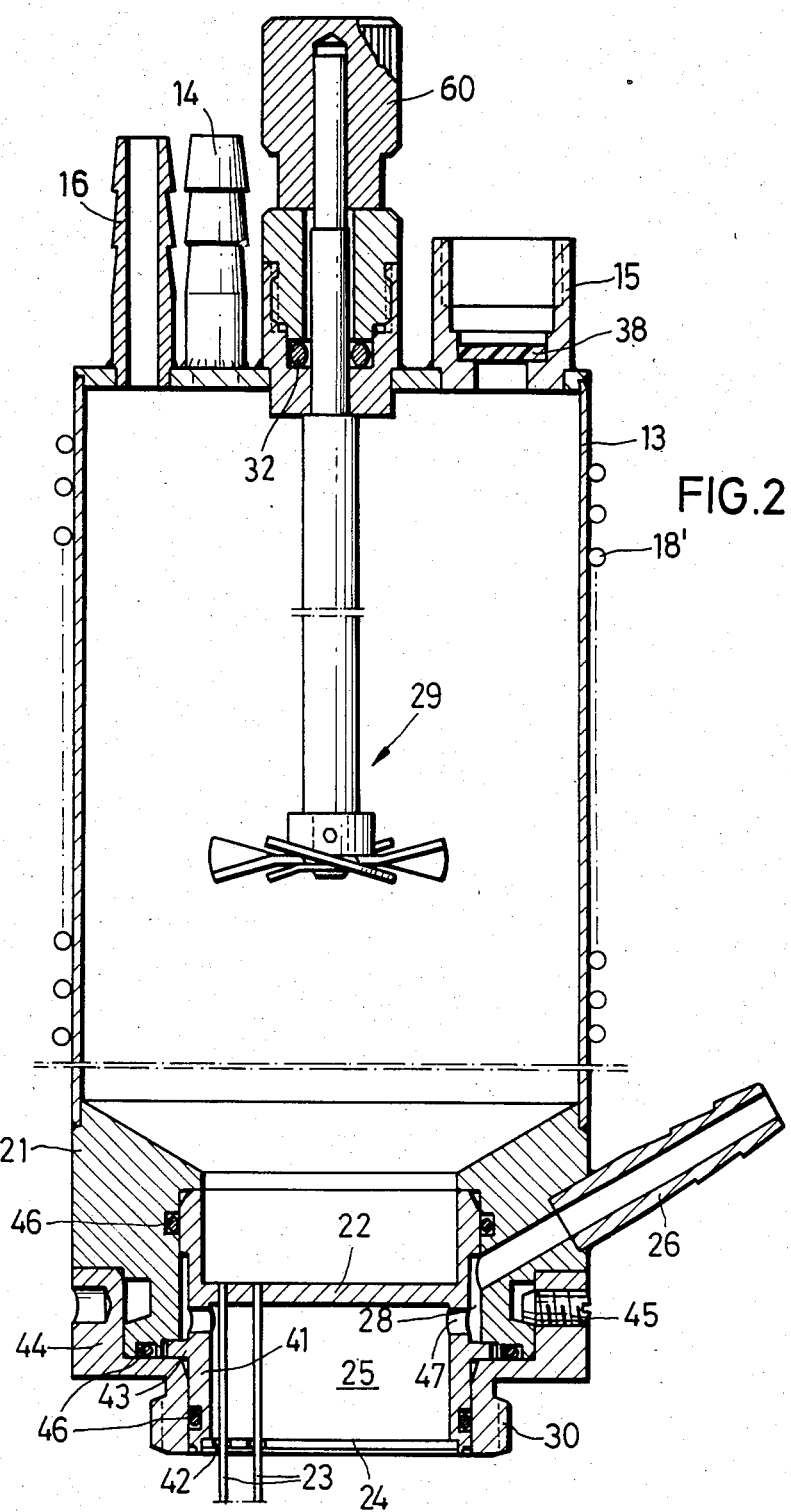
FIG. 2 shows a longitudinal section through a different embodiment of an immobilization vessel.

The immobilization vessel shown in FIG. 2 differs only insignificantly from that shown in FIG. 1 or outlines the constructional details of the latter in greater detail. The pierceable septum 38 consisting of an elastomeric material is recognizable in the inocculating nozzle 15 while the locking cap has been removed. The shaft of the agitator 29 extends through a passage sealed with a packing 32 from the upper end wall of the vessel 13 to the outside and connected there with a manually rotatable rotary knob 60. The heater 18' consists of a heater coil wound helically about the vessel 13.

The block 21 which is welded to the lower end of the vessel 13 contains an axial bore into which a substantially tubular insert 41 is fitted. The perforated plate 22 is formed by a partition wall of the insert 41, and the lower plate 24 constitutes the lower conclusion of the insert 41. The outflow openings 42 surrounding the discharge pipes can also be seen in FIG. 2. The insert 41 is provided with a circular flange 43 which is fitted in a step-shaped recess at the lower end of the block 21. From the downward side presses against the flange 43 a hasp cap 44 which is attached to the block 21 with radial setscrews 45 under axial tension.

The annular space 28 which surrounds part of the length of the insert 41 consists of an annular recess at the circumference of the insert 41. The sealing of the annular space 28 is effected by annular packings 46. Radial bores 47 extend from the annular space 28 into the pressure chamber 25 through which the discharge pipes 23 are passed paraxially.

First of all, the technique of the immobilization is described hereinafter in general.

A supporting substance such as a viscous polyelectrolyte solution (alginate, pectinate, carboxymethyl cellulose, carrageenane, furcellarane, cellulose sulfate, chitosan, etc.), a polymer solution capable of gelling (Curdlan, agar, agarose, gelatin etc.) or a non-aqueous polymer solution (cellulose acetate, polystyrene, Eudragit, etc.) is mixed with the enzymes, cell organella or whole cells. This mixture is then introduced or pumped into the temperable immobilization vessel 10 and brought under pressure. The pressure is preselected by a pressure gauge, and the gas flows through the sterile filter 17. The mixture is added dropwise through the thin discharge pipes 23 and into the solution of the cross-linking agent or the reprecipitation bath and, in doing so, biocatalyst beads are formed momentarily. The lateral lower pressure junction 26 is connected through the sterile filter 27 and a pressure gauge to a pressure line. This gas stream flows past the steel tubes and, in doing so, prematurely tears off the drops having formed at the edges of the discharge pipes 23. It is possible to adjust the size of droplets exactly by the selection of the pressure in the pressure chamber 25. Beads having a narrow distribution of radii are obtained.

Figure 3:
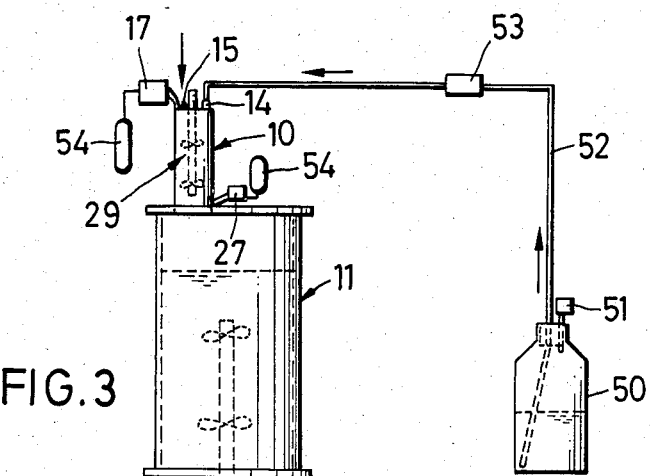
FIGS. 3 to 5 are diagrammatic representations of various kinds of use of the apparatus.
Figure 4:
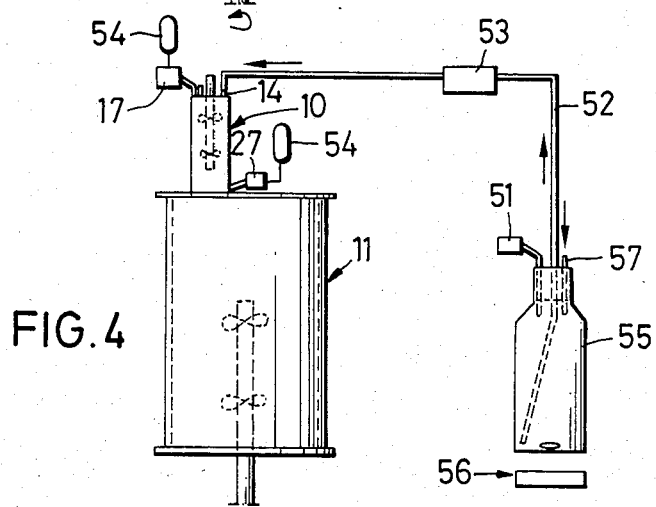
Figure 5:
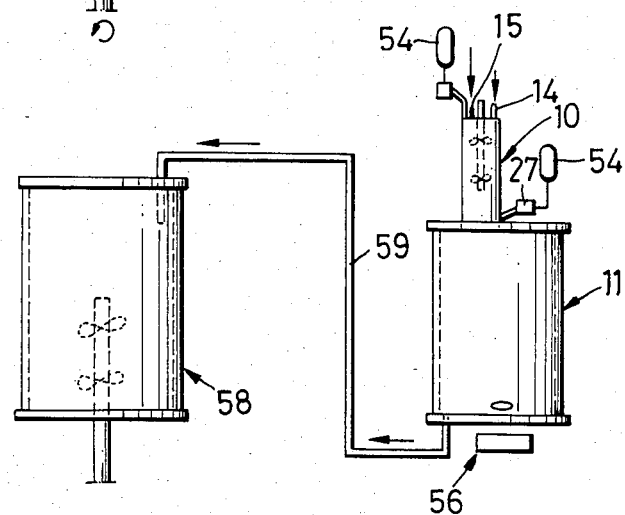

Various working procedures which may be carried out with the use of the apparatus are illustrated by FIGS. 3 to 5.

In case of the working procedure shown in FIG. 3, the immobilization vessel 10, the collecting vessel 11 and the starile filters 17 and 27 are jointly sterilized first of all. The supporting substance is contained in a sterile bottle 50 which is equipped with a sterile filter 51 for aeration. From the bottle 50 extends a tubing 52 through a pump 53, e.g. a hose pump, to the feed nozzle 14 of the immobilization vessel 10. The pump pumps the supporting substance into the immobilization vessel, and the microorganisms or enzymes are added through the inocculating nozzle 15. Both of the substances are mixed by means of the agitator 29. Thus, the collection vessel 1 is used at the same time as a fermentation vessel. The gas pressure sources connected to the sterile filters 17 and 27 are referred to as 54 in FIGS. 3 to 5.

The working sequence represented in FIG. 4 differs from that shown in FIG. 3 by the fact that the supporting substance and the enzymes, cell organella or whole cells are mixed in an external vessel 55 which is provided with a magnetic stirrer 56 and thereafter pumped through the tubing 52 and the pump 53 through the feed nozzle 14 into the immobilization vessel 10. The vessel 55 is provided with an inlet connection 57 for feeding the enzymes or microorganisms. The contents of the vessel 55 may be pumped into the immobilization vessel 10 either batchwise or continuously. Thus, it is possible to process a volume which is greater than that of the immobilization vessel. In case of the continuous production of beads, the separate application of pressure 17 may, if necessary or desired, be dispensed with.

The immobilization vessel 10 and the collecting vessel 11 which is used as a fermenter are jointly sterilized together with the starile filters 17 and 27 also case of the working procedure represented in FIG. 4. The sterilization of the vessel 55 containing the supporting substance and of the transfer system 52,53 is effected separately herefrom.

In case of the working procedure represented in FIG. 5, there is provided a separate fermentation vessel 58 into which the immobilized microorganisms or enzymes are transferred through a tubing line 59 from the collecting vessel 11. For this purpose, the collecting vessel 11 is provided at its bottom wall with a connection nozzle for the tubing 59. The supporting substance is filled into the feed nozzle 14 of the immobilization vessel 10, and enzymes, microorganisms or the like are introduced by inocculation through the inocculating nozzle 15. The collecting vessel 11 contains the solution of the cross-linking agent or the reprecipitation bath. After the biocatalyst beads have formed in the collecting vessel 11, the beads are sucked off from the bottom of the collecting vessel and transferred through the tubing 59 and into the fermentation vessel.

Two immobilization examples carried out in accordance with the working procedure represented in FIG. 4 will be described hereinafter.

1. In alginate

To 400 ml of a sterile 3.5% Na alginate solution (Protonal LF 20/60) were added 100 ml of an acetobacter sp. cell suspension having a wet biomass proportion of 80 g. and well suspended. This suspension was thereafter transferred into the immobilization apparatus having been described. By applying pressure (1.4 bars) by means of sterile air, the suspension was added dropwise through the steel tubes into a 2% $CaCl_2$ cross-linking agent solution contained in the collecting vessel. In doing so, Ca alginate biocatalyst beads were momentarily formed. The sterile air steam used to blow off the beads was selected in such a manner that beads having a diameter of 1.2 mm were obtained After.a cross-linking time of 30 minutes, the biocatalyst beads were used to produce gluconic acid from oxygen and glucose. The resultant biocatalysts had an activity of 3.88 U/g KFM with a residual activity of 48%.

2. In chitosan

To 400 ml of a sterile 1.1% chisosan acetate solution (chitosan-hv) were added 100 ml of an *E. coli* cell suspension having a wet biomass proportion of 50 g and well suspended. This suspension was thereafter transferred into the immobilization apparatus having been described. By applying pressure (1.3 bars) by means of sterile air, the suspension was added dropwise through the steel tubes into the 2% Na tripolyphosphate cross-linking agent solution (pH 8). The sterile air stream used to blow off the beads was selected such that beads having a final diameter of 0.6 mm were obtained. After the complete cross-linking throughout, curing and shrinkage of the chitosan biocatalyst beads, they could be used directly for the cleavage of Penicillin G to form 6-aminopenicillanic acid and phenylacetic acid. The resultant biocatalyst beads had an activity of 60 U/g KFM with a residual activity of 63%.

What is claimed is:

1. In an apparatus for the production of biocatalyst beads which includes:
   an immobilization vessel which has an upper region and a lower region, said immobilization vessel being sealed in a germproof manner;
   at least one nozzle means for filling said immobilization vessel, said nozzle means being associated with said immobilizaton vessel upper region;
   discharge means associated with said immobilization vessel lower region, said discharge means comprising a pressure chamber defined by a top member and a bottom member, with said bottom member being provided with a plurality of discharge openings, a plurality of discharge pipes, each discharge pipe penetrating the top member for communication with the interior of the immobilization chamber and coaxially passing through one of said discharge openings in said bottom member;
   a collecting vessel for containing a solution of a cross-linking agent or a reprecipitation bath, said collecting vessel having an upper region arranged beneath the lower region of said immobilization vessel;
   the improvement comprising:
   a connecting nozzle surrounding all of said discharge pipes and forming part of the lower region of said immobilization vessel;
   said collecting vessel being sealed in a germproof manner;
   means located in the upper region of said collecting vessel receiving said connecting nozzle whereby the interior of said immobilization vessel and the interior of said collecting vessel are in communication via said discharge pipes; and
   means providing a germproof seal between said connecting nozzle and said means receiving said connecting nozzle.

2. An apparatus as recited in claim 1 wherein said collecting vessel is a fermenter and includes agitation means in the interior thereof.

3. An apparatus as recited in claim 1 wherein said collecting vessel is a fermenter and includes heater means.

4. An apparatus as recited in claim 1 wherein said collecting vessel is a fermenter and includes agitation means in the interior thereof and heater means.

5. An apparatus as recited in claim 1 wherein said discharge means further comprises:
   an annular insert having an annular side wall and an associated top plate and a bottom plate spaced a distance below said top plate defining said pressure chamber;
   detachable mounting means detachably mounting said annular insert in the lower region of said immobilization vessel;
   said top plate being perforated by a plurality of holes with each hole receiving the top end of one of said discharge pipes; and
   said bottom plate being provided with said discharge openings having passing there through said discharge pipes.

6. An apparatus as recited in claim 5 wherein said mounted annular insert defines with said discharge means an annular space surrounding said mounted annular insert side wall;
   passage means disposed in said annular side wall for providing fluid communication between said annular space and said pressure chamber;
   a compressed gas source; and
   means for connecting said compressed gas source in fluid communication with said annular space.

7. An apparatus as recited in claim 1, 5 or 6 wherein said discharge pipes protrude into the interior of said collecting vessel.

8. An apparatus as recited in claim 1, 5 or 6 wherein the upper region of said collecting vessel has a cover, said cover is provided with an opening receiving said connecting nozzle, and said discharge pipes protrude into the interior of said collecting vessel beneath said cover.

9. An apparatus as recited in claim 1, 5 or 6 wherein said immobilization vessel is provided with agitator means in the interior thereof.

10. An apparatus as recited in claim 9 wherein said immobilization vessel is provided with heater means.

11. An apparatus as recited in claim 1, 5 or 6 wherein said immobilization vessel is provided with heater means.

12. An apparatus as recited in claim 1, 5 or 6 wherein innoculating nozzle means are associated with the upper region of said immobilization vessel and said innoculating nozzle means includes a pierceable septum.

13. An apparatus as recited in claim 10 wherein innoculating nozzle are associated with the upper region of said immobilization vessel and said innoculating nozzle means includes a pierceable septum.

14. An apparatus as recited in claim 13 wherein said collecting vessel is a fermenter and includes agitation means in the interior thereof and heater means.

* * * * *